United States Patent
Majeed

(10) Patent No.: US 6,689,400 B2
(45) Date of Patent: Feb. 10, 2004

(54) PROCESS OF OBTAINING COMPOSITIONS OF STABLE LUTEIN AND LUTEIN DERIVATIVES

(75) Inventor: Muhammed Majeed, Piscataway, NJ (US)

(73) Assignee: Sabinsa Corporation, Piscataway, NJ (US)

( * ) Notice: Subject to any disclaimer, the term of this patent is extended or adjusted under 35 U.S.C. 154(b) by 0 days.

(21) Appl. No.: 10/058,827

(22) Filed: Jan. 30, 2002

(65) Prior Publication Data

US 2003/0018222 A1 Jan. 23, 2003

Related U.S. Application Data

(60) Provisional application No. 60/264,722, filed on Jan. 30, 2001.

(51) Int. Cl.[7] .................... A61K 35/78; A61K 9/00; A61K 47/00; B01J 41/00
(52) U.S. Cl. .............. 424/778; 424/439; 424/489; 424/400; 210/660; 210/669; 210/732
(58) Field of Search ................. 424/439, 778, 424/489; 210/660, 669, 732

(56) References Cited

U.S. PATENT DOCUMENTS

| 3,998,753 | A | * | 12/1976 | Antoshkiw et al. ........... 516/58 |
| 4,048,203 | A | * | 9/1977 | Philip ......................... 554/208 |
| 4,929,774 | A | * | 5/1990 | Fukumachi et al. ......... 568/824 |
| 5,382,714 | A | * | 1/1995 | Khachik ...................... 568/834 |
| 5,536,504 | A | * | 7/1996 | Eugster et al. .............. 424/450 |
| 5,648,564 | A | * | 7/1997 | Ausich et al. ............... 568/834 |
| 6,007,856 | A | * | 12/1999 | Cox et al. .................... 426/250 |

OTHER PUBLICATIONS

Sapozhnikov et al., Blocking of the light reaction by hydroxylamine in the transform of xanthophylls. Doklady. Akad. Nauk. SSSR., 127, 1128–1131; Chem Abstr., 54, 11162 (1959).*
Sies et al., Antioxidant functions of vitamins. Vitamins E and C, beta–carotene, and other carotenoids. Ann. N.Y. Acad. Sci., 669, 7–20 (1992).*
Chew et al., Effects of lutein from marigold extract on immunity and growth of mammary tumors in mice. Anticancer Res., 16, 3689–3694 (1996).*
Jyonouchi et al., Immunomodulating actions of carotenoids: Enhancement of in vivo and in vitro antibody production to T–dependent antigens. Nutr. Cancer, 21 (1), 47–58 (1994).*
Shi et al. Stability of lutein under various storage conditions. Nahrung, 44, 38–41 (1997).*

* cited by examiner

Primary Examiner—Thurman K. Page
Assistant Examiner—Simon J. Oh
(74) Attorney, Agent, or Firm—Arent Fox Kintner Plotkin & Kahn, PLLC

(57) ABSTRACT

The present invention concerns methods of obtaining stable lutein and its derivatives. Additionally, the invention concerns various compositions comprising lutein, lutein esters, tetrahydrocurcuminoids, and carnosic acid.

40 Claims, 7 Drawing Sheets

| Index | Induction Time (Hr.) | Antioxidant |
|---|---|---|
| Control (lard only) | 2.32 | |
| Zea¹utein | 3.10 | 1.34 |

Zealutein has some antioxidant activity against lipid peroxidation.

FIGURE 1

| Index | Induction Time (Hr.) | Antioxidant |
|---|---|---|
| Control (lard only) | 2.32 | |
| Zealutein | 3.10 | 1.34 |

Zealutein has some antioxidant activity against lipid peroxidation.

FIGURE 2

ZEALUTEIN (XENOGARD) REGULAR (GRANULES)

Stability Data of batch No. C11315

| Period of keeping | Storage condition: RT(30-33° C) Assay in % | | Storage Condition: 40° C/RH 75% Assay in % | | Remarks |
|---|---|---|---|---|---|
| | Lutein | Zeaxanthin | Lutein | Zeaxanthin | |
| Initial | 8.20 | 1.19 | 8.2 | 1.19 | 90 days stable |
| 30 days | 8.13 | 1.20 | 7.99 | 1.16 | |
| 60 days | 8.12 | 1.16 | 7.96 | 1.11 | |
| 90 days | 6.48 | 1.12 | 5.04 | 1.08 | |

This is stable for three years under normal condition

FIGURE 3

ZEALUTEIN BJ – 80 MESH

STABILITY STUDIES

Stability Data of batch No. C11293

| Period of keeping | Storage condition: RT(30-33° C) Assay in % | | Storage Condition: 40° C/RH 75% Assay in % | | Remarks |
|---|---|---|---|---|---|
| | Lutein | Zeaxanthin | Lutein | Zeaxanthin | |
| Initial | 8.5 | 1.27 | 8.5 | 1.27 | 60 days stable |
| 30 days | 7.80 | 1.22 | 7.74 | 1.20 | |
| 60 days | 7.24 | 1.19 | 6.82 | 1.12 | |
| 90 days | 4.82 | 1.15 | 3.93 | 1.12 | |

This is stable for two years under normal condition

FIGURE 4

FINISHED PRODUCT SPECIFICATION

STANDARDS AND LIMITS

ZEALUTEIN™ - BJ (80 MESH)
(1% ZEAXANTHIN, 5% LUTEIN, 2% PIPERINE)

| | |
|---|---|
| Description | Orange to orange red powder with characteristic odour. |
| Identification | To comply by HPLC |
| Loss on drying | Not more than 5.0% |
| Solubility | Partly soluble in acetone and in chloroform, sparingly soluble in alcohol, insoluble in water. |
| Ash content | Not more than 10.0% |
| Heavy metals | Not more than 20ppm |
| Arsenic | Not more than 1ppm |
| Lead | Not more than 10ppm |
| Tapped Bulk Density | Between 0.40g/ml and 1.0g/ml |
| Loose Bulk Density | Between 0.35g/ml and 0.70g/ml |
| Sieve Test (passes through) | |
| -80 mesh | Not less than 95.0% |
| Assay by HPLC | |
| -Content of Zeaxanthin | Not less than 1.0% |
| -Content of Lutein | Not less than 5.0% |
| -Content of Piperine | Not less than 2.0% |
| -Content of other Carotenoids | |
| Content of other Carotenoids by UV (Esters of Capsanthin, Capsorubin, Zeaxanthin, β-Carotene and Cryptoxanthin) | Not less than 1.0% |

FIGURE 5

FINISHED PRODUCT SPECIFICATION

STANDARDS AND LIMITS

ZEALUTEIN™-REGULAR
(1% ZEAXANTHIN, 5% LUTEIN, 2% PIPERINE)

| | |
|---|---|
| Description | Brick red granular powder with characteristic odour. |
| Identification | To comply by HPLC |
| Loss on drying | Not more than 5.0% |
| Solubility | Partly soluble in acetone and in chloroform, sparingly soluble in alcohol, insoluble in water. |
| Ash content | Not more than 10.0% |
| Heavy metals | Not more than 20ppm |
| Arsenic | Not more than 1ppm |
| Lead | Not more than 10ppm |
| Tapped Bulk Density | Between 0.40g/ml and 1.0g/ml |
| Loose Bulk Density | Between 0.35g/ml and 0.70g/ml |
| Sieve Test (passes through) | |
| -20 mesh | Not less than 100.0% |
| -40 mesh | Not less than 60.0% |
| -80 mesh | Not less than 30.0% |
| Assay by HPLC | |
| -Content of Zeaxanthin | Not less than 1.0% |
| -Content of Lutein | Not less than 5.0% |
| -Content of Piperine | Not less than 2.0% |
| Content of other Carotenoids by UV (Esters of Capsanthin, Capsorubin, Zeaxanthin, β-Carotene and Cryptoxanthin) | Not less than 1.0% |

FIGURE 6

Table 1

Effect of topical application of zealutein on 12-O-tetradecanoylphorbol-13-acetate (TPA)-induced edema of mouse ears

| Treatment | Number of mice per group | Weight Per ear punch (mg) | Percent inhibition |
|---|---|---|---|
| Experiment 1 | | | |
| 1. Acetone | 4 | 6.46±0.15 | - |
| 2. TPA (1 nmol) | 5 | 15.30±0.87 | - |
| 3. TPA (1 nmol) + zealutein (0.04 mg) | 4 | 10.93±0.77 | 49.9 |
| 4. TPA (1 nmol) + zealutein (0.12 mg) | 4 | 8.89±0.69 | 72.7 |
| 5. TPA (1 nmol) + zealution (0.36 mg) | 4 | 7.88±0.23 | 84.0 |
| Experiment 2 | | | |
| 1. Acetone | 6 | 6.69±0.20 | - |
| 2. TPA (1 nmol) | 11 | 13.70±0.61 | - |
| 3. TPA (1 nmol) + zealutein (0.04 mg) | 6 | 10.53±0.42 | 45.2 |
| 4. TPA (1 nmol) + zealutein (0.12 mg) | 6 | 8.57±0.35 | 73.2 |
| 6. TPA (1nmol) + zealutein (0.36 mg) | 6 | 7.71±0.31 | 85.5 |
| 7. TPA (1 nmol) + curcumin (0.04 mg) | 6 | 10.50±0.70 | 45.6 |
| 8. TPA (1 nmol) + curcumin (0.12 mg) | 6 | 7.40±0.31 | 89.9 |
| Experiment 3 | | | |
| 1. Acetone | 5 | 6.61±0.25 | - |
| 2. TPA (1 nmol) | 5 | 14.61±0.77 | - |
| 3. TPA (1 nmol) + lutein (0.072 mg) | 5 | 10.04±0.57 | 57.1 |
| 4. TPA (1 nmol) + lutein (0.36 mg) | 5 | 8.81±0.37 | 72.5 |

Female CD-1 mice (25-28 days old) were treated topically on both ears with 20 µl acetone, TPA (1 nmol), or TPA (1 nmol)) together with test compound in 20 µl acetone. Five hours later, the mice were killed by cervical dislocation and ear ounches were weighed. Dat aare expressed as the mean±SE.

FIGURE 7
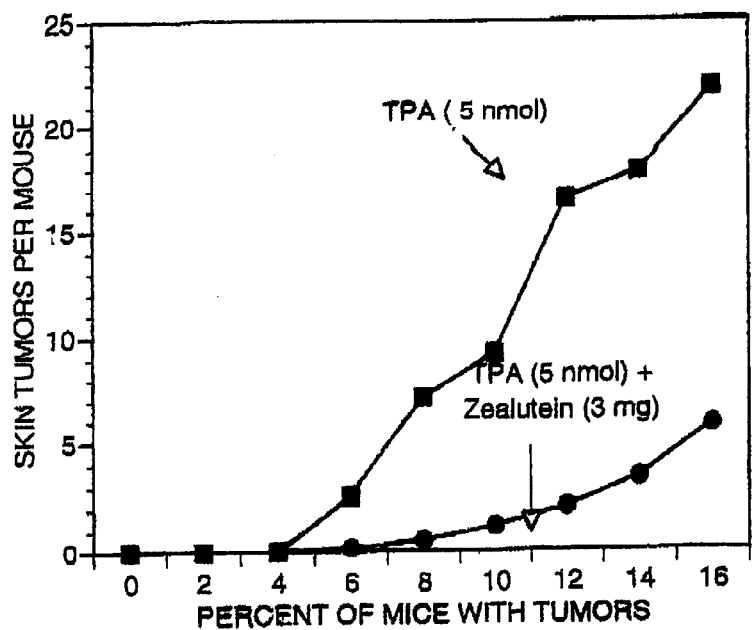
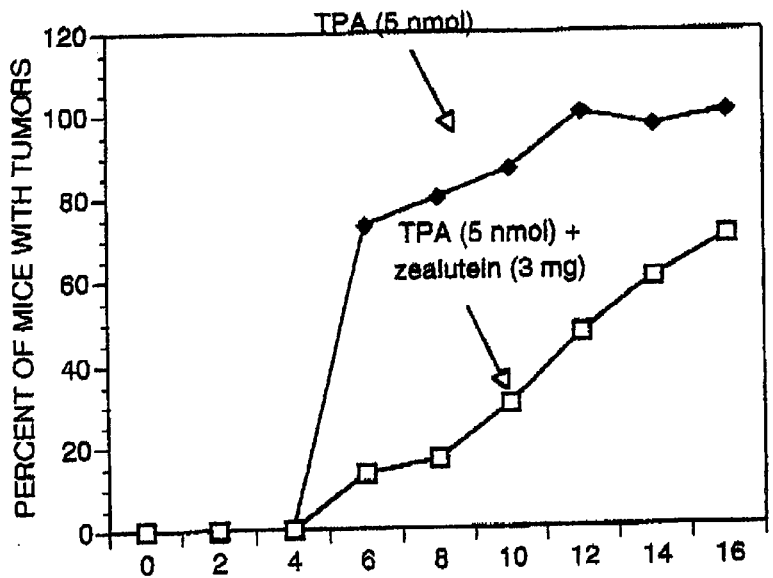
TOPICAL APPLICATION OF TPA (WEEKS)

FIGURE 8

Inhibitory effect of zealutein on 12-O-tetradecanoylphorbol-13-acetate (TPA)-induced skin tumor promotion in CD-1 mice previously initiated with 7,12-dimethylbenz[a]anthracene (DMBA)

| Group | Treatment | Number of mice per group | Body weight per mouse (g) | Percent of mice with tumors | Tumors per mouse | Tumor volume tumor (mm³) | Tumor volume per mouse (all mice) (mm³) | Number of tumors diameter (> 5 mm) |
|---|---|---|---|---|---|---|---|---|
| 1 | DMBA + Acetone | 30 | 31.7±0.6 | 100.0% | 0 | 0 | 0 | 0 |
| 2 | DMBA + TPA (5nmol) | 16 | 32.5±0.7 | 100.0% | 21.8±2.0 | 7.7±1.2 | 176.8±25.1 | 20 |
| 6 | DMBA + Zealutein | 16 | 32.2±0.6 | 87.5% (-12.5%) | 5.8±1.4 (-73.4%) | 6.6±3.8 (-14.3%) | 22.7±7.7 (-87.2%) | 0 (-100%) |

Female CD-1 mice (7-8 weeks old; 30 mice per group) were initiated with a single dose of 7,12-dimethylbenz[a]anthracene (DMBA). One week later, the mice were promoted with 200 μl acetone, TPA (5 nmol) in 20 μl acetone or TPA (5 nmol) + zealutein (3 mg) in 200 μl acetone for 16 weeks. Data are expressed as mean ± SE.

PROCESS OF OBTAINING COMPOSITIONS OF STABLE LUTEIN AND LUTEIN DERIVATIVES

This application claims the benefit of U.S. Provisional Application No. 60/264,722, filed Jan. 30, 2001.

BACKGROUND OF THE INVENTION

Lutein is a carotenoid found in fruits and vegetables which has begun to acquire importance as a nutraceutical because of its antioxidant and immunomodulating/immunostimulating actions. These actions are manifested in its ability to reduce oxidative stress and/or depression of the immune system, in conditions such as age-related macular degeneration, cataracts, atherosclerosis, and some forms of cancer. Also, because of its yellow to red coloration and natural occurrence in human foods, lutein also is used as a food colorant.

Lutein suitable for nutraceutical and cosmetic uses can be found in the chromoplasts of flowers, fruits and roots (such as, but not limited to, carrots and yellow potatoes). Lutein is typically present in plant chromoplasts as long chain fatty esters, typically diesters, of acids such as palmitic and myristic acids, e.g. lutein dipalminate, lutein dimyristate and lutein monomyristate. It has also been noted that once lutein is isolated from the plant, the lutein is biologically active in either the ester form or in the free form.

Additionally, the highly unsaturated unconjugated chain of caroteinoids that makes up lutein is very sensitive to air, oxidizing agents, reducing agents, and structural alterations. Therefore, the loss of lutein during storage is well known. Further, lutein loss has been shown to begun as early as the raw material handling stage of the process. It has been documented that under carefully controlled conditions exposure to white fluorescent light resulted in the degradation of lutein in the range of 0.8–10.7% per day (please see Nahrung, 44, 38–41). However, ascorbic acid, an alkaline pH, low temperature (4° C.) and darkness were found to retard the degradation of carotenoids, including lutein (please see Akad. Nauk. SSSR., 127, 1128–1131; Chem Abstr., 54, 11162). It has also been discovered that lutein and lutein esters are not stable compounds at room temperature or higher, and that free lutein is especially vulnerable to chemical and biological deterioration.

The preparation of stable and biologically active lutein and/or its esters from natural sources, such as Marigold petals, presents a challenging task. As seen in the following discussion, many patents have been issued on a method of obtaining such esters and the composition of the same.

U.S. Pat. No. 5,382,714 (hereinafter the "'714 patent") discloses a method of isolating, purifying and recrystallizing substantially pure lutein, preferably from saponified marigold oleoresin in its pure free form, apart from chemical impurities and other carotenoids. It also discloses that as of the filing of the '714 patent, pure lutein suitable for human use had not been commercially available for use as a chemopreventative agent in clinical trials. It was also noted that pure lutein which is free of chemical contaminant is necessary to design and conduct proper human intervention studies.

The '714 patent noticed that esterified luteins are found with fatty acids in marigold petals, and that lutein could be produced upon saponification of the marigold lutein esters. However, the resulting lutein product was impure as it was contaminated with numerous chemical impurities.

The '714 patent disclosed a method of removing the lutein from the marigold petals without the chemical impurities. This method is disclosed as comprising the purification, preferably of a saponified marigold extract through the use of a series of filtrations and water/alcohol washes to obtain crude lutein crystals. These crystals are then dissolved in a halogenated organic solvent in which lutein is strongly soluble and then in a second organic solvent in which lutein is only partly soluble. This mixture is then cooled and the lutein is recrystallized in a high purity and it is then filtered and dried under vacuum.

U.S. Pat. No. 5,648,564 (hereinafter the "'564 patent") discloses a process for forming, isolating and purifying xanthophyll crystals, preferably lutein, from marigold flower petals. It further disclosed that a xanthophyll diester-containing plant extract is saponified in a composition of propylene glycol and aqueous alkali to form xanthophyll crystals. It was also stated that the crystallization is achieved without the use of added organic solvents. The resulting crystals are then isolated and purified to produce substantially pure xanthophyll crystals suitable for human consumption.

The '564 patent also noted that the claimed method had several advantages over the prior art, including its ability to produce luteins suitable for human consumption without using relatively toxic organic solvents during the isolation or crystallization steps. Additionally, the method does not require a recrystallization step.

U.S. Pat. No. 4,048,203 (hereinafter the "'203 patent") discloses a process for the purification of lutein-fatty acid esters from marigold flower petals or marigold petal oleoresins based on alkanol precipitation.

U.S. Pat. No. 6,007,856 (hereinafter the "'856 patent") discloses oil-in-water dispersions of $\beta$-carotene and other carotenoids that are stable against oxidation. The dispersions are prepared from water-dispersible beadlets comprising higher concentrations of colloidal $\beta$-carotene.

U.S. Pat. No. 3,998,753 (hereinafter the "'753 patent") discloses water dispersible carotenoid compositions in liquid or powder form which can be incorporated into pharmaceuticals, cosmetic preparations or animal foodstuffs. It also discloses the processes of preparing these dispersible cartenoid compositions.

U.S. Pat. No. 4,929,774 (hereinafter the "'774 patent") discloses a stable mixture of an oxidation-sensitive compound which also comprises triglycerides, complexing agents and coating substances.

U.S. Pat. No. 5,536,504 (hereinafter the "'504 patent") discloses methods for treating tumors with ultramicroemulsions from spontaneously dispersible concentrates containing xanthophyll esters, and new esters with xanthophyll compounds. Further, methods for the production of the concentrates are also disclosed.

SUMMARY OF THE INVENTION

This invention relates to methods of producing lutein and lutein derivatives in a stable form as well as the individual compounds. Additionally, the invention is directed towards specific lutein derivatives which possess a long storage life.

DETAILED DISCLOSURE

Prior to the discoveries of this invention, those of ordinary skill used antioxidant vitamins and/or beadlets to stabilize lutein. These previously used methods primarily prevented the oxidation and the chemical and biological degradation of the lutein. One way in which the present invention is novel is that its stabilization of lutein and its esters goes beyond preventing oxidation. The present invention not only prevents oxidation of lutein and lutein esters, it also protects the lutein compound from destabilizing factors such as oxidants, temperature, humidity, daylight, and UV rays (hereinafter "other factors") by obtaining lutein and lutein esters which protect against the other factors. It is also noted that these factors effect the stability of lutein and lutein esters during the extraction process, as well as the industrial processing of the same for use in final products. Finally, it was noted that vitamin-based antioxidants can prevent the deterioration of lutein, but it was not known whether they would be effective against the other factors.

The present invention provides a method of protecting lutein against direct and indirect physical, chemical, and biological factors which contribute to the deterioration of lutein and lutein esters. This method protects lutein and lutein esters from both xenobiotic compounds and the environmental elements. The totality of the protective action of the method is referred to hereinafter as XENOGARD (see Table I). The method of the present invention is two-fold. It is based on a unique process of isolation, which provides lutein and lutein esters chemically and less physically stressed in their isolated forms. The resulting product of the XENOGARD method is also more resistant to chemical/biological deterioration. Additionally, the invention provides a method of combining lutein and lutein esters with at least one stabilizing compound, such as, but not limited to, 0.01–10 wt % tetrahydrocurcuminoids, 0.01–10 wt % of curcuminoids, or 0.01–10 wt % carnosic acid.

It should be noted that tetrahydrocurcuminoids and curcuminoids are phenolic in nature, and that they are also recognized as antioxidants which provide protection against free radicals and also prevent the generation of free radicals. Additionally, curcuminoids are known to absorb UV rays and to protect pharmaceutical preparations from physiochemical deterioration. Curcuminoids have also been found to prevent pyrolysis which is the high temperature related deterioration of processed food and nutrients. Curcuminoids are also recognized for their anti-microbial properties in preventing the growth of bacteria or fungi, which is a factor that is detrimental to the stability of lutein and lutein esters especially in humid conditions. Tetracurcuminoids, which are derivatives of curcuminoids, are particularly effective in scavenging free radicals and are also complementary to the action of curcuminoids which are primarily effective in preventing free radicals from occurring in biological systems. Carnosic acid is compatible and complementary with both curcuminoids and tetracurcuminoids. It is an antioxidant and anti-microbial compound similar to curcuminoids and tetracurcuminoids' broad action consisting of free radical prevention and scavenging action.

The process of obtaining XENOGARD lutein and lutein esters proceeds as follows. First, marigold flower petals are harvested. These petals are then shade dried, crushed and left at room temperature for a period of time, preferably 3 to 4 hours. The resulting material is then treated with a solvent, preferably an alcohol, and more preferably ethyl alcohol, and incubated, preferably for 5 hours at room temperature. A preferable ratio of solvent to marigold flower petals is 100 kg of the marigold material to 400 L of ethyl alcohol. Following the incubation period, the resulting solution is collected. This procedure is then repeated, preferably at least two additional times, and the combined alcohol extracts are combined. If the process is repeated two times and the preferred ratio is used then the total solution should amount to about 1250 L. The extracts are then diluted with water to obtain an alcohol solution, which is preferably 70% by weight alcohol.

Alternatively, the shade dried petals can be treated with supercritical carbon dioxide for a period of time, preferably 10 hours, and after the evaporation of the carbon dioxide occurs, the remaining oleoresin is diluted with an alcohol, preferably ethanol, and water, as described above, to obtain a diluted alcohol solution, preferably a 70% alcohol solution.

This extract of marigold petals in the alcohol solution may then used to obtain lutein esters or free lutein by subjecting the extract to hydrolysis. This process entails passing the oleoresin in the alcohol solution through a column packed with an anion exchange resin. Preferably, this is performed at a rate of 20–50 L per hour. Suitable resins include Amberjet 4200(cl), Amberlite IRA 410, Amberlite IRA 900, Dowex 1x2-100, Dowex 22cl, Dowex Marathon A2, Dowex MSA 1, Dowex 550 A, all of which are Rohm-Haas or Dow products.

Upon completion of the hydrolysis, the eluents are collected and diluted with deionized water with a strong and vigorous agitation. The resulting lutein crystals are filtered, collected, and dried in vacuum with the exclusion of oxygen.

These lutein crystals or lutein esters can be combined subsequent to their isolation with a stabilizing mixture of tetrahydrocurcuminoids in an amount of 0.01–10.0 wt %, curcuminoids in an amount of 0.01–10.0 wt %, and carsonic acid in an amount of 0.01–10.0 wt % to form the XENOGARD composition. Preferably each of the stabilizing ingredients are present in an amount of 0.1 wt. %. The XENOGARD composition of lutein or esters of lutein are then packaged under nitrogen atmosphere, sealed, and stored until further use. An additional XENOGARD compositions of lutein and lutein esters can be prepared in the form of a soft extract comprising at least 50 wt % marigold oleoresin, 45 wt % vegetable oil (preferably refined Soya oil), 1.5 wt % citric acid, and 2 wt % natural tocopherol.

The XENOGARD lutein and lutein esters can be further stabilized by a coating process. An example of such a coating process would involve combining a sugar, preferably sucrose, preferably in as slurry form, with water (preferably distilled water) and the XENOGARD composition to obtain a uniform blend. Preferably, the ratio used in forming the uniform blend would entail 450 g of sucrose to 100 ml of distilled water to 250 mg of the XENOGARD composition. Starch is then added to the uniform blend and the resulting mixture is then charged to a mixer which is run until the mixture is blended, preferably 30 minutes. Also, the preferred ratio used in determining the appropriate amount of starch to add is 630 g of starch to 800 g of the uniform blend. PVP (preferably in a ratio 450 g to 1430 g of starch solution) combined in a solvent (preferably 70% ethanol solution) is then added to the starch solution and blended to form a dough with a preferred moisture content of less than 5%, adjusted at 30° C. under vacuum. The dough is then fed into a granulator preferably fitted with a 30 mesh screen and the granules are collected in trays which have been preferably lubricated with talc and dried under a vacuum for 8–12 hours. The dried granules are then transferred to a coating pan (suitably approximately 350 g of PVP and 40 g of paprika resin). The resulting granules are dried again under vacuum at 30° C. for about 6–8 hours, and sifted and packed.

An example of a XENOGARD product is Zealutein®. Zealutein® is comprised of lutein, zexanthin, piperine (Bioperine®)), other carotenoids, and other stabilizing components. FIG. 1 proves Zealutein®'s antioxidant activities, whereas FIGS. 2 and 3 illustrate its stability in two different forms. Further, it has been shown that the Zealutein®

Regular Granules are stable for three years under normal conditions, whereas Zealutein® BJ-80 Mesh is stable for two years under normal conditions. The composition of both of these forms of Zealutein® are disclosed in FIGS. 4 and 5. However, the final composition of Zealutein® comprises lutein in an amount not less than 5 weight percent of the final product, Zeaxanthin in an amount not less than 1 weight percent of the final product, Piperine (and prefereably Bioperin®) in an amount not less than 2 weight percent of the final product, and other carotenoids in an amount not less than 1 weight percent of the final product.

Additionally, further stabilizing components which may be used in the present invention include other carotenoids in the form of Capsanthin ester, Capsorubin ester, Zeaxanthin ester, Cryptoxanthin exter, and beta-carotene ester. These stabilizing components may be 1–10 weight percent of the final product. Additionally, paprika carotenoids are a potential source of stabilizing components, provided the paprika carotenoids are in the form of esters. Additions to the stabilizing components may also be added. These added compounds include tetracurcuminoids, Rosmarinic acid, green tea catechins and other similar natural antioxidants.

DRAWINGS

FIG. 1: FIG. 1 illustrates the Rancimat testing of Zealutein® and shows that Zealutein® possesses antioxidant properties.

FIG. 2: FIG. 2 illustrates a comparison of Zealutein® Regular Granules against lutein in which the stability of each has been tested at 30 day intervals in conditions of 40° C. and 75% relative humidity.

FIG. 3: FIG. 3 illustrates a comparison of Zealutein® BJ-80 Mesh against lutein in which the stability of each has been tested at 30 day intervals in conditions of 40° C. and 75% relative humidity.

FIG. 4: FIG. 4 lists the requirements and composition for Zealutein® BJ-80 Mesh.

FIG. 5: FIG. 5 lists the requirements and composition for Zealutein® Regular Granules.

FIG. 6: FIG. 6 illustrates the results of testing the effect of a topical application of zealutein on 12 O-tetradecanoylphorbol-13-acetate (TPA)-induced edema of mouse ears.

FIG. 7: FIG. 7 illustrates the dramatic difference in the percent of mice with cancer when being treated with a topical application of TPA when one group is treated with TPA alone and another is treated with TPA and zealutein.

FIG. 8: FIG. 8 illustrates the results of testing the inhibitory effect of zealutein on 12 O-tetradecanoylphorbol-13-acetate (TPA)-induced skin tumor promotion in CD-1 mice previously initiated with 7,12-dimethylbenz[a]anthracene (DBMA).

REFERENCES CITED

Sies, H., Stahl, W., Sundquist, A. R. (1992) Antioxidant functions of vitamins. Vitamins E and C, beta-carotene, and other carotenoids. Ann. N.Y. Acad. Sci., 669, 7–20.

Chew, B. P., Wong, M. W., and Wong, T. S. (1996) Effects of lutein from marigold extract on immunity and growth of mammary tumors in mice. Anticancer Res., 16, 3689–3694.

Jyonouchi, H., Zhang, L., Gross, M. and Tomita, Y. (1994) Immunomodulating actions of carotenoids: Enhancement of in vivo and in vitro antibody production to T-dependent antigens. Nutr. Cancer, 21(1), 47–58.

Shi, X. M. and Chen, F. (1997) Stability of lutein under various storage conditions Nahrung, 44, 38–41.

Sapozhnikov, D. I., Eidelman, Z. M., Bazhanova, N. V., and Popova, O. F. (1959) Blocking of the light reaction by hydroxylamine in the transformation of xanthophylls. Doklady. Akad. Nauk. SSSR., 127, 1128–1131; Chem Abstr., 54, 11162.

U.S. Pat. No. 5,382,714
U.S. Pat. No. 5,648,564
U.S. Pat. No. 4,048,203
U.S. Pat. No. 6,007,856
U.S. Pat. No. 3,998,753
U.S. Pat. No. 4,929,774
U.S. Pat. No. 5,536,504

What is claimed is:

1. A process for producing a stabilized lutein composition comprising:
   a) shade drying marigold flower petals;
   b) extracting the dried marigold flower petals of step a) with a solvent to produce an extract solution;
   c) passing the extract solution through a column packed with an anion exchange resin to obtain an eluent;
   d) diluting the eluent to form a diluted solution;
   e) and recovering lutein crystals from the diluted solution.

2. The process of claim 1, wherein the shade drying of the marigold petals is performed at room temperature for 3 to 4 hours.

3. The process of claim 2, wherein step b) is performed in the proportion of 400 L of ethyl alcohol to 100 kg of dried marigold petals and wherein step b) further comprises incubating the mixture of dried flower petals and ethyl alcohol for 5 hours at room temperature.

4. The process of claim 3, wherein the solvent of step b) is an alcohol.

5. The process of claim 4, wherein the alcohol of step b) is ethyl alcohol.

6. The process of claim 3, wherein step b) further comprises draining the mixture of ethyl alcohol and dried marigold petals and collecting the liquid in an appropriate container, repeating the procedure at least one additional time with the same marigold petals, and diluting the collected liquid with sufficient amounts of water to obtain a 70% alcohol solution.

7. The process of claim 1, wherein the eluent of step d) is diluted with deionized water.

8. The process of claim 1, further comprising the drying of the recovered lutein crystals in a vacuum and the packing of the dried lutein crystals in a nitrogen atmosphere.

9. The process of claim 8, further comprising, prior to the packing step, combining the lutein crystals with at least one of tetrahydrocurcuminoids in an amount of 0.001–0.1 wt %, curcuminoids in an amount of 0.001–0.1 wt % and carnosic acid in an amount of 0.001–0.1 wt % to form a further stabilized composition.

10. The process of claim 9, further comprising prior to the packing step:
   i) combining a sucrose slurry with the further stabilized composition in a ratio of one part of the further stabilized composition to 1–10 parts of sucrose to form a uniform blend;
   ii) adding 10 parts of starch to the uniform blend of step i) to form a starch mixture; and
   iii) adding an ethanol solution of poly(vinyl pyrrolidone) in an amount of 1 part of poly(vinyl pyrrolidone) to 0.1–10 parts of the further stabilized composition, and drying the resulting mixture to the starch mixture of step ii) to form an ethanol starch mixture.

11. The process of claim 10, further comprising:
iv) forming the ethanol starch mixture granules and collecting the granules in trays lubricated with talc and drying the granules in a vacuum; and
v) transferring the dried granules to a coating pan, drying the dried granules in a vacuum, sifting said dried granules and packing the dried granules.

12. The process of claim 11, wherein the coating pan of step v) is coated with poly(vinyl pyrrolidone) and paprika resin in a proportion of approximately 9 parts of poly(vinyl pyrrolidone) to 1 part of paprika resin.

13. A process for producing a stabilized lutein composition comprising:
a) shade drying marigold flower petals;
b) treating the dried marigold flower petals of step a) with supercritical carbon dioxide;
c) allowing the supercritical carbon dioxide to evaporate to leave an oleoresin;
d) passing an alcohol solution of the oleoresin through a column packed with an anion exchange resin; and
e) collecting lutein crystals from the eluent.

14. The process of claim 13, wherein the marigold flower petals are dried at room temperature for 3 to 4 hours.

15. The process of claim 14, wherein dried marigold flower petals are treated with supercritical carbon dioxide for 10 hours.

16. The process of claim 13, wherein the alcohol solution is a 70% alcohol solution.

17. The process of claim 13, further comprising packaging the collected lutein crystals under a nitrogen atmosphere.

18. The process of claim 13, further comprising, prior to the packing step, combining the lutein crystals with at least one of tetrahydrocurcuminoids in an amount of 0.001–0.1 wt %, curcuminoids in an amount of 0.001–0.1 wt % and carnosic acid in an amount of 0.001–0.1 wt % to form a further stabilized composition.

19. The process of claim 18, further comprising prior to the packing step:
i) combining a sucrose slurry with the further stabilized composition in a ratio of one part of the further stabilized composition to 1–10 parts of sucrose to form a uniform blend;
ii) adding 10 parts of starch to the uniform blend of step i) to form a starch mixture; and
iii) adding an ethanol solution of poly(vinyl pyrrolidone) in an amount of 1 part of poly(vinyl pyrrolidone) to 0.1–10 parts of the further stabilized composition, and drying the resulting mixture to the starch mixture of step ii) to form an ethanol starch mixture.

20. The process of claim 19, further comprising:
iv) forming the ethanol starch mixture granules and collecting the granules in trays lubricated with talc and drying the granules in a vacuum; and
v) transferring the dried granules to a coating pan, drying the dried granules in a vacuum, sifting said dried granules and packing the dried granules.

21. The process of claim 20, wherein the coating pan of step v) is coated with poly(vinyl pyrrolidone) and paprika resin in a proportion of approximately 9 parts of poly(vinyl pyrrolidone) to 1 part of paprika resin.

22. A composition comprising at least one of lutein and lutein esters and at least one stabilizing compound selected from the group consisting of tetrahydrocurcuminoids, curcuminoids, and carnosic acid.

23. The composition of claim 22, wherein said composition comprises lutein or lutein esters in an antioxidant effective amount, and tetrahydrocurcuminoids, curcuminoids, and carnosic acid each in a proportion of 0.01–10.0 wt %.

24. The composition of claim 22, wherein said composition comprises lutein or lutein esters in a biologically effective amount and tetrahydrocurcuminoids, in a proportion of 0.01–10.0 wt %.

25. The composition of claim 22, wherein said composition comprises lutein or lutein esters in a biologically effective amount and curcuminoids in a proportion of 0.01–10.0 wt %.

26. The composition of claim 22, wherein said composition comprises lutein or lutein esters in a biologically effective amount and carnosic acid in a proportion of 0.01–10.0 wt %.

27. The composition of claim 22, wherein said composition comprises lutein or lutein esters in a biologically effective amount and tetrahydrocurcuminoids, curcuminoids, and carnosic acid each in a proportion of 0.01–10.0 wt %.

28. The composition of claim 22, wherein said composition comprises lutein or lutein esters, tetrahydrocurcuminoids, curcuminoids, and carnosic acid each in equal amounts.

29. A composition comprising a soft extract composed of marigold oleoresin obtained from exposing shade dried crushed marigold petals to supercritical carbon dioxide, vegetable oil, citric acid, and natural tocopherol, each in an amount of 0.5–5.0% by weight.

30. The composition of claim 29, wherein said vegetable oil is refined Soya oil.

31. A composition comprising lutein in an amount of not less than 5.0% by weight, Zeaxanthin in an amount of not less than 1.0% by weight, piperine in an amount of not less than 1.0% by weight, and other carotenoids in an amount of not less than 1.0% by weight.

32. The composition of claim 31, wherein said composition further comprises one or more stabilizing components selected from the group consisting of zeaxanthin ester, cryptoxanthin ester, and beta-carotene ester in an amount of not less than 1.0% by weight, but no more than 10.0% by weight.

33. The composition of claim 31, wherein said composition further comprises one or more stabilizing components selected from the group consisting of paprika carotenoid esters, tetrahydrocurcuminoids, rosmarinic acid, and green tea catechins in an amount of not less than 1.0% by weight, but no more than 10.0% by weight.

34. The composition of claim 31, wherein said composition comprises zeaxanthin in an amount of not less than 1.0% by weight, lutein in an amount of not less than 5.0% by weight, piperine in an amount of not less than 1.0% by weight, and at least one ester of capsanthin, capsorubin, zeaxanthin, beta-carotene, or cryptoxanthin in an amount of not less than 1.0% by weight.

35. The composition of claim 34, wherein piperine is present in an amount of not less than 2.0% by weight.

36. A XENOGARD composition, wherein said composition comprises lutein in an amount of not less than 5.0% by weight, Zeaxanthin in an amount of not less than 1.0% by weight, piperine in an amount of no more than 1.0% by weight, and other carotenoids in an amount of not less than 1.0% by weight.

37. The composition of claim 22, wherein said at least one stabilizing compound is a mixture of 0.1 wt % tetrahydrocurcuminoids, 0.1 wt % curcuminoids and 0.1 wt % carsonic acid.

38. A composition comprising at least 50 wt % marigold resin, 45 wt % vegetable oil, 1.5 wt % citric acid, and 2 wt % natural tocopherol, wherein said marigold resin comprises at least one of lutein and lutein esters.

39. The composition of claim 38, wherein said vegetable oil is refined Soya oil.

40. The composition of claim 31, wherein piperine is present in an amount of not less than 2.0% by weight.

* * * * *